United States Patent [19]

Barbier et al.

[11] Patent Number: 4,465,069
[45] Date of Patent: Aug. 14, 1984

[54] CRANIAL INSERTION OF SURGICAL NEEDLE UTILIZING COMPUTER-ASSISTED TOMOGRAPHY

[76] Inventors: Jean Y. Barbier, 7532 Warner Ave., St. Louis, Mo. 63117; Christopher J. Moran, 12559 Amersham Ct., St. Louis, Mo. 63141

[21] Appl. No.: 505,893

[22] Filed: Jun. 20, 1983

Related U.S. Application Data

[60] Continuation of Ser. No. 270,404, Jun. 4, 1981, abandoned, which is a division of Ser. No. 111,892, Jan. 14, 1980, Pat. No. 4,360,028.

[51] Int. Cl.$^3$ ............................................. A61B 19/00
[52] U.S. Cl. ................................. 128/303 B; 128/659
[58] Field of Search ........................... 128/303 B, 659; 378/208, 209

[56] References Cited

U.S. PATENT DOCUMENTS 4,131,802 12/1978 Braden et al. ...................... 378/208
4,228,799 10/1980 Anichkov et al. ............... 128/303 B
4,341,220 7/1982 Perry ........................... 128/303 B X

FOREIGN PATENT DOCUMENTS 2139433 2/1973 Fed. Rep. of Germany ... 128/303 B

Primary Examiner—Michael H. Thaler
Attorney, Agent, or Firm—Jerome A. Gross

[57] ABSTRACT

The head of a patient is held in place horizontally on the indexable sliding cradle of an X-ray scanner by a vertical ring encircling the head having radiolucent rests supporting the head behind the ears at the mastoid processes and beneath the eyes at the cheekbone area. Adjustable horizontally-projecting instrument support structure is carriage-mounted on an arcuate track in the ring between the forward rests and has a horizontally-bored instrument guide-holder of such density as to appear on an X-ray scan and positionable adjacent to the head with its horizontal bore in the plane of any indexable scanning section of the X-ray scanner. By scanning the head and adjacent guide holder, the holder may be positioned with its bore in the same plane as and on a line directed to a point of interest in the brain. Thereafter, the holder may be utilized to guide a surgical needle to the point of interest.

5 Claims, 5 Drawing Figures

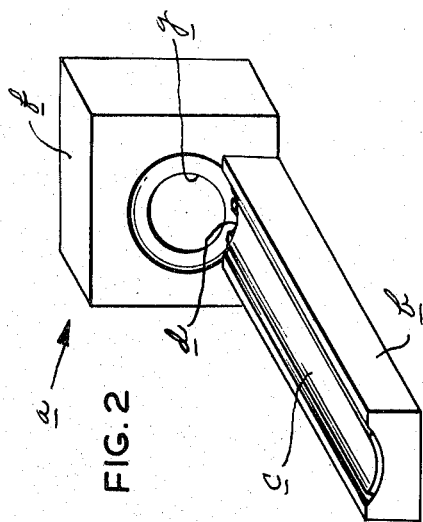
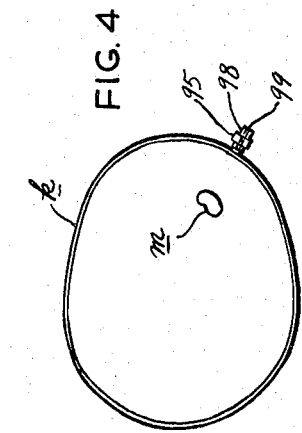
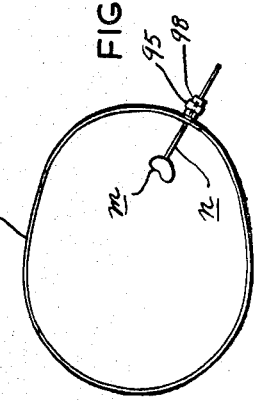
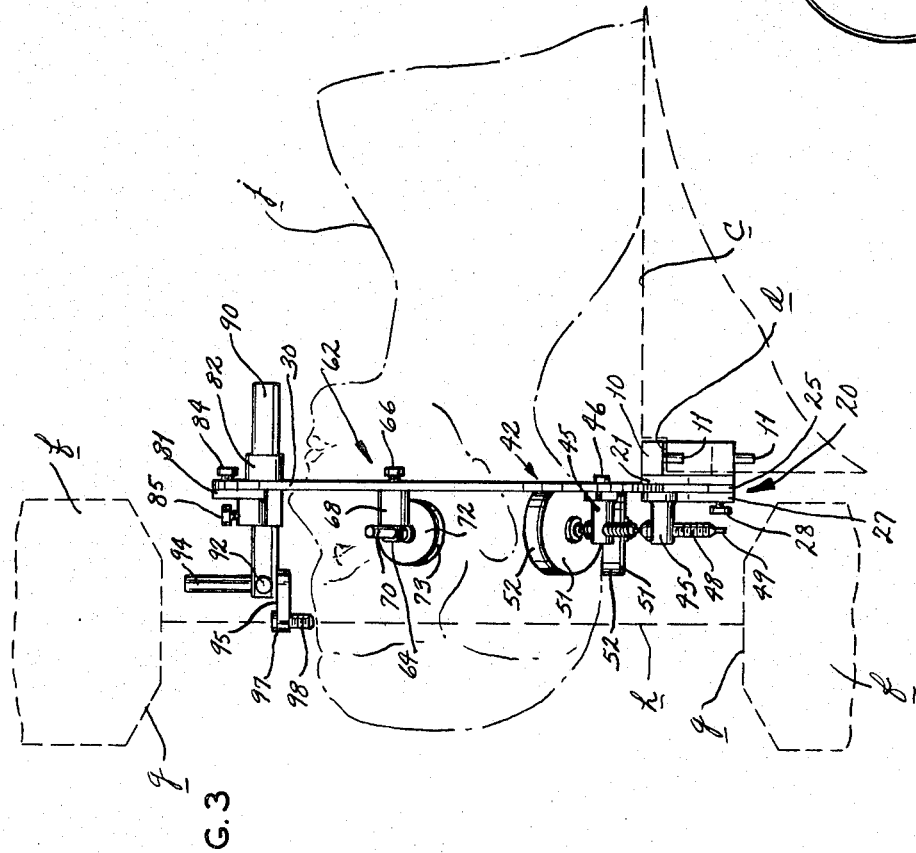

CRANIAL INSERTION OF SURGICAL NEEDLE UTILIZING COMPUTER-ASSISTED TOMOGRAPHY

This is a continuation of application Ser. No. 270,404 filed June 4, 1981 now abandoned, which is a division of application Ser. No. 111,892, filed Jan. 14, 1980, now U.S. Pat. No. 4,360,028.

BACKGROUND OF THE INVENTION

The present invention relates to surgical procedures in which small medical instruments, generally needles, are inserted through bone or other tissue to a particular point of interest, with a minimum of disturbance. More specifically, the invention may relate to insertion of a needle through the skull to a point of interest within the brain, such as a lesion or tumor, for aspiration biopsy or decompression.

Representations of parallel planar sections of human tissue, such as horizontal sections taken through the brain, may be made by a computed-tomography scanner. Various tomographic techniques make possible study of tumors, lesions, or other points of interest.

Surgical procedures performed on the brain at such points of interest may be done by insertion of needles or other slender instruments through a bore in the skull, but these procedures heretofore have been difficult because the surgeon had no simple and direct way to insert the instrument directly to the point of interest. This limitation often dictated use of the alternative technique of a craniotomy, to permit visual inspection of the point of interest.

SUMMARY OF THE INVENTION

The object of the present invention is to provide a simple and direct way by which a medical instrument may be precisely guided to a point of interest within the brain, or other portion of the body, by utilizing a computer-assisted tomography scanner.

Briefly summarized, a patient is horizontally supported on the cradle of such a scanner with his head secured within a ring vertically mounted to the cradle, whose precise horizontal positioning makes possible representations of an indexable plurality of parallel vertical sections through the upper part of the head. The head is held in place relative to the ring by a pair of radiolucent rests behind the ear at the mastoid processes and another pair beneath the eyes at the maxilla or zygomatic arches, leaving the entire upper portion of the head unobstructed for purposes of the scanner. Adjustable instrument support structure is carriage-mounted on an arcuate track between the rests at the front of the head, projecting perpendicularly from the plane of the ring toward the top of the head. The support structure includes a horizontally bored guide-holder preferably of a plastic whose density as hereafter described, is substantially of the order of that of soft body tissue, positionable with the bore in the plane of any vertical scanning section.

After preliminarily scanning to determine the index of the scanning plane in which the point of interest is found, the support structure is adjusted to position the axis of the guide-holder bore in the plane of interest and also locate it angularly along the ring and direct its bore through a desired point of entry into the skull along a line leading to the point of interest. Another scan confirms the position of the guide-holder bore relative to the point of interest. After incision of the skin at the point of passage through the skull, the guide-holder bore provides a guide for drilling through the skull. Then a needle or other surgical instrument may be inserted in the plane of interest through the aligned guide-holder bore and skull bore, with its depth determined by repeated scanning and adjustment unit it is properly positioned to the point of interest. The desired surgical procedure may then be performed.

BRIEF DESCRIPTION OF THE DRAWINGS

FIG. 2 is a schematic isometric view of a typical computer-assisted tomography scanner and being of the type with which the apparatus of FIG. 1 is adapted to be used, having a horizontally-movable and indexable cradle.

FIG. 3 is a side view of the apparatus of FIG. 1 mounted to the cradle of the FIG. 2 scanner, shown in dashed lines, and supporting the head of a patient, shown in phantom lines, in position for scanning. For clarity, the instrument holding provision is shown rotated 90° from its FIG. 1 position.

FIG. 4 is a schematic representation of a typical scan when utilizing the present invention, showing a section of the head and the guide-holder of the present invention positioned with its bore in the plane of the scan and directed to a lesion or other point of interest within the skull.

FIG. 5 is a view similar to FIG. 4, with a needle inserted through the bore of the guide-holder and through the skull into the brain to the point of interest.

DESCRIPTION OF THE PREFERRED EMBODIMENT

Figure 1:
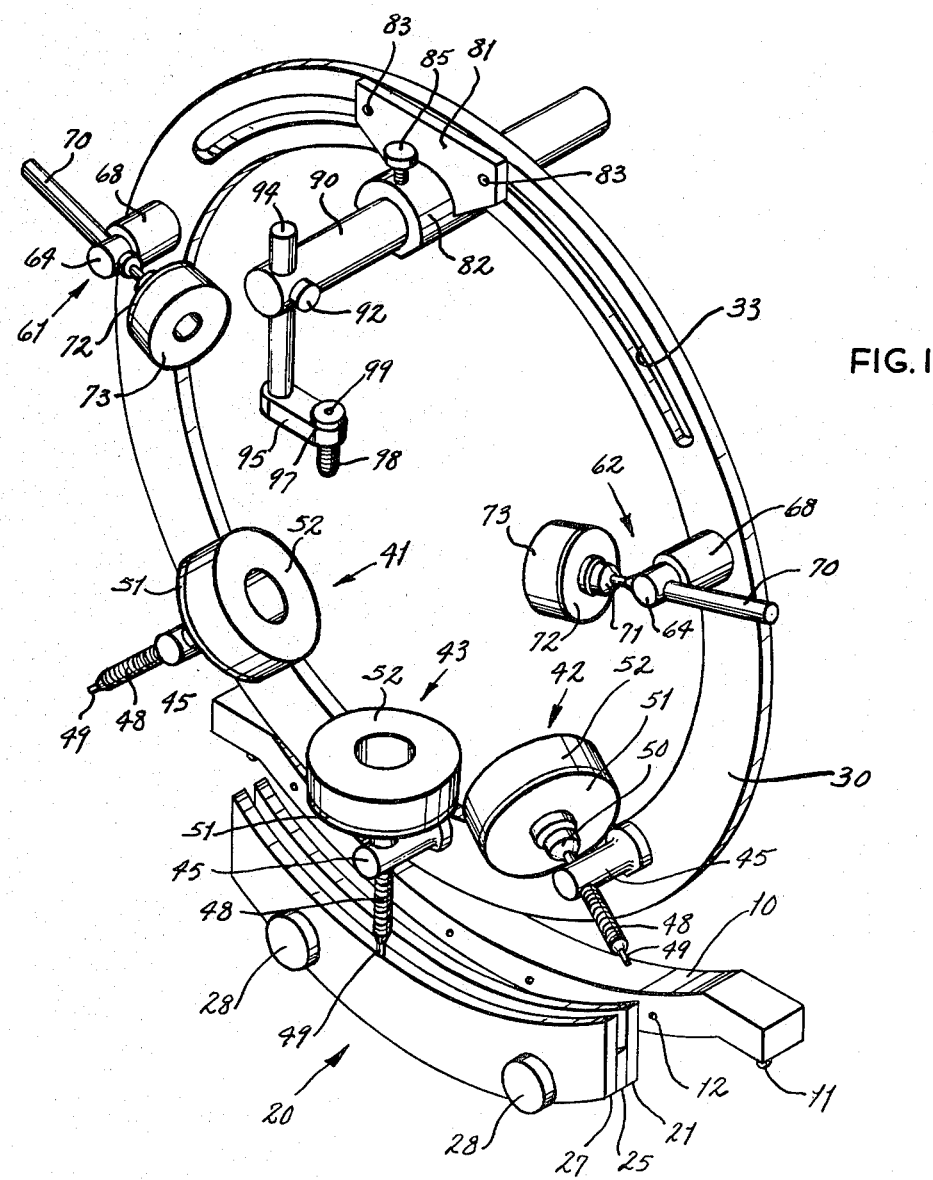
FIG. 1 is an isometric projection of a preferred embodiment of the apparatus of the present invention.

In the present invention, scanning equipment utilizing computerized tomography aids in directing a surgical needle to a point of interest within the body of a patient. In the preferred embodiment, the insertion is of a needle through the skull to a point of interest within the brain, though the invention may be applicable to uses within the neck, the chest cavity, the long bones of the body, or to other points of interest, especially those not easily accessible because of overlying bones or delicate organs.

In the present invention, the scanner, generally designated a, is of the type shown in FIG. 2, having a table b, including a patient-supporting movable cradle c forming a support with a longitudinal axis. The cradle c has a transverse vertically-bored concave-downward head restraint mount d at one of its ends, as shown in FIGS. 2 and 3. At one end of the table b the scanner a has an scanning mechanism f having a horizontally-extending circular throat g, sufficiently large to receive the head of a reclining patient. The vertical scanner throat g is at such a level that the head restraint end of the movable cradle c may be slid axially therein, so that the patient's head may be moved horizontally to an indexed position within the scanner throat g when the patient is reclined on the table b. The scanner f is of the type having an X-ray tube, not shown, and corresponding opposing receptors revolving about the scanner throat g in a scanning plane h, shown by the dashed lines in FIG. 3. Digital information processing equipment, along with a cathode ray tube display, not shown, utilize the projections to produce representations of the parallel planes transverse to the head by tomographic techniques.

In developing a scan, the X-ray tube and corresponding receptors, as they revolve about the scanner throat g, obtain a great quantity of density information. The raw data received from the receptors is received and compiled by the computer to produce attenuation coefficients for a matrix of points in the scanning plane h, including a patient's head positioned within the scanner throat g. Typically, these attenuation coefficients may be arranged on a scale from negative to positive 1,000, known as the Hounsfield scale, for which −1,000 is the attenuation coefficient for air, zero is the attenuation coefficient for water, and +1,000 is the attenuation coefficient for dense bone. For purposes of reference, the Hounsfield number for brain tissue, which is considered a soft tissue, is approximately 30. Since the densities of points of interest within the brain may be only slightly different than that of normal brain tissue, for example, an increase from 30 to 33 on the Hounsfield scale, only a portion of the scale can be utilized to achieve the required contrast. Accordingly, the information processing equipment is utilized to assign the grey scale of the CRT display to a desired range within the Hounsfield scale. For example, to study brain tissue, it may be appropriate to select a "window" of 100 about a center "level" of 30 on the Hounsfield scale. In such a representation, all tissue denser than Hounsfield number +80 appears as solid white, and all material less dense than Hounsfield number −20 appears as black. Materials with densities between appear as varying shades on the grey scale. The "level" and/or the "window" may be changed instantly by adjusting the equipment, permitting the surgeon to search for those density differences which appear only with greater or lesser sensitivities or at different "levels".

In the preferred embodiment of the present inventive apparatus, a patient's head may be supported within the scanner throat g, as shown in FIG. 3, by head-holding apparatus comprising a ring-like member or ring 30 encircling the head, forming frame-like patient restraint means, securable to the movable cradle c on the scanner table b. A ring mount, generally designated 20, clamps the lower end of the ring 30 and an adaptor 10 pin-mounts the ring mount 20 to the head restraint mount d of the cradle c.

The adaptor 10, shown in FIGS. 1 and 3, has a concave-downward lower side, matable with the head restraint mount d of the movable cradle c of the scanner a; a plurality of downward-extending pins 11 on the adaptor lower side are matable with corresponding bores in the head restraint mount d. The upper side of the adaptor 10 presents an upward arcuate concave edge in a plane perpendicular to the longitudinal axis of the needle c. A plurality of horizontal threaded bores 12 are provided in the side of the adaptor 10, for mounting the ring mount 20 to the adaptor 10. The construction of the head restraint mount d may vary with different scanner models; thus, a suitable adaptor may be used for each.

The ring mount 20, shown in FIGS. 1 and 3, is made up of an arcuate front plate 21, a similar arcuate back plate 27, and an intermediate arcuate spacer 25 of lesser depth sandwiched between the front and rear plates 21, 27 at their lower sides, the spacer thickness being substantially the same as or somewhat less than the ring 30. The arcuate front plate 21 has a plurality of adaptor mounting bores alignable with the threaded bores 12 of the adaptor 10, to receive stud bolts for mounting the adaptor 10 to the front plate 21. The back plate 27 and spacer 25 have a plurality of aligned bores, aligned with a plurality of threaded bores in the front plate 21. Thumbscrews 28 extend through the bores in the back plate 27 and spacer 25 to the front plate threaded bores, to mount these three parts together to form an adjustable width arcuate concave upward-opening slot with which to clamp the ring 30 upright in a chosen angular position between the front plate 21 and back plate 27, upward of the spacer 25.

The ring 30 is, in the preferred embodiment, constructed of one-fourth inch thick aluminum plate having approximately a fourteen inch diameter circular outer edge, smaller than the scanning throat; the outer edge of at least its lower portion is interengageable with the slot in the ring mount 20. The upper portion of the planar ring 30 has an arcuate slot or track 33 through it extending approximately 55 degrees to each side of center. The arcuate track 33 provides angular range of positions at which to affix a carriage-mounted instrument support structure, described below. The interior dimensions of the ring 30 are sufficient to accommodate a patient's head.

At about 18 degrees upward of the level of its center, as shown in FIG. 1, the ring 30 has a pair of mounting bores for the upper head rests, one bore at each side of the ring 30, spaced downward of the end of the slot 33. Correspondingly, the ring 30 has three mounting bores for the lower rests, one of its vertical centerline, and the other two about 45 degrees upward therefrom.

The three identical lower adjustable head supports or rests, each on the same side of the ring 30, are hereafter generally designated as the left lower support 41, the right lower support 42 and the center lower support 43. Each is made up of a standard 45 having a flared end with a threaded concentric bore by which the standard 45 is mounted to the lower rest mounting bores by a mounting bolt 46. The opposite end of the standard 45 has a threaded bore, perpendicular to the axis of the standard 45, which receives a threaded shaft 48 having a flattened finger grip portion 49 at one end and a ball and socket joint 50 at its opposite end. The ball and socket joint 50 mounts to a thin, circular arcylic plastic plate 51, which carries a substantially radiolucent foam rubber donut-shaped cushion 52.

Two identical adjustable upper head supports or rests are utilized, the left rest generally designated 61 and the right rest generally designated 62, both on the same side of the ring 30 as the lower supports 41, 42, 43. Each has a standard 64 with a reduced diameter threaded end extending through one of the upper rest mounting bores to a thumbnut 66. At its opposite end, the standard 64 has a bore, perpendicular to its axis, receiving a shaft 70, which has a ball and socket 71 at one of its ends, mounted to a similar thin circular acrylic plastic plate 72 carrying similar foam rubber cushions 73. A tubular spacer 68 on the standard 45 between the bore and the ring 30 clamps the shaft 70 when the thumbnut 66 is tightened.

The preferred embodiment if further comprised of a carriage 80, preferably of cast aluminum, slidably mounted to the arcuate track 33. The carriage 80 is formed of a substantially triangular plate portion 81 parallel to the ring 30 at whose apex is a perpendicular tubular portion 82 on the inner side of the ring 30. The triangular plate portion 81 has a pair of threaded bores 83 which receive thumbscrews 84 which extend through the slot or track 33 and provide for both sliding within and clamping to the slot 33. Perpendicular to its axis, the tubular portion 82 has a threaded bore carrying a thumbscrew 85.

A cylindrical arm 90 is received by the tubular portion 82, thereby extending perpendicular to the plane of the ring 30, and is slidably adjustable by loosening the thumbscrew 85. That end of the arm 90 which extends to the side of the ring 30 has a large bore perpendicular to its axis, and a smaller threaded bore with a thumbscrew 92 perpendicular to and extending into the large bore. The larger bore accepts a circular riser post 94 having at its end a perpendicular instrument guide-holder 95, preferably made of a three-eighths inch thick plastic plate which extends from the riser post 94 to an opposite end having a threaded bore 97 parallel to the axis of the riser post 94. The threaded bore 97 accepts an exteriorly-threaded instrument guide 98, having a small concentric bore 99 which will accept a surgical instrument such as a needle or drill bit. Several replaceable instrument guides having various internal bore diameters may be provided, to accept needles of different sizes, as well as a twist drill bit for boring through the skull. An instrument guide 98 utilized to guide a twist drill is provided with an outer lip at one end, to prevent the drill bit from turning the guide 98 from its position within the guide-holder bore 97.

The drill guide 98 and guide-holder 95 are made of material having such a density as to be visible on a scan by the scanner. Therefore it may thus be of a density in the range at which the scanner utilized operates, for example, one which falls on the Hounsfield scale between the density of air and dense bone. For greater convenience, the drill guide 98 and guide-holder 95 of the preferred embodiment are made of material having a density substantially on the order of magnitude of the density of soft body tissue but slightly greater than that of the brain tissue under study, preferably such as in the range of 50 to 200 on the Hounsfield scale, though materials having Hounsfield numbers as high as 400-500 may be utilized, depending upon the relative dimensions of the material. In the preferred embodiment, an acrylic plastic, specifically polymethylmethacrylate, manufactured and sold under the trademark PLEXIGLASS and having a Hounsfield number believed to be approximately 100-150, is utilized, though other acrylic plastics or other materials could be substituted. Since this plastic has a density greater than that of brain tissue (which has a Hounsfield number of approximately 30), it appears on a typical scan of the brain as solid white on scan representations having a small grey scale "window", such as 50 or 100, and having a "level" of near 30, while causing substantially no artifacts. To avoid severe artifacts in the scan, other parts of the apparatus, such as the arm 90 and riser post 94, may be of the same material, or of a material of lesser density, such as that of the radiolucent cushions 52, 73.

In use of the apparatus of the preferred embodiment, the specific adaptor 10 for the make and model of scanner to be utilized is mounted to the ring mount 20. Then the downward pins 11 of the adaptor 10 are fitted into the head restraint mount d of the removable cradle c, and the ring 30 is mounted and clamped to the ring mount 20 by tightening the thumbscrews 28. A patient j then reclines on the cradle c with his head encircled by the ring 30, as shown in FIG. 3. The lower rests 41, 42, 43 are adjusted by turning the threaded shaft 48 until the head is approximately centered within the ring 30, with the left and right rests 41, 42 supporting the head behind the ears substantially at the mastoid processes, and the center rest 43 supporting the back of the neck. Next the thumbnuts 66 for the top support rest 60 are loosened and the shafts 70 are pushed inward to press the foam rubber cushions 73 against the cheekbone areas of the head beneath the eyes, either at the maxilla or the zygomatic arches, and the thumbnut 66 is tightened, clamping the shaft 70 in place. The head is thus fixedly supported on the cradle c of the X-ray scanner a by the opposed rests, at a chosen angular position determined by the angular setting of the ring 30 in the clamping slot of the ring mount 20. By the reproduceable positioning of the cradle c, the patients's head is indexable to any position within the scanner throat g. Preliminary scans of the head may then be performed at successive sections, and the index number for the position of the cradle at which the point of interest within the brain is in the scanning plane noted.

Next, the surgeon will determine the best straight-line path for the needle through the skull and brain to the point of interest and its point of entrance through the skull is marked on the skin of the head. Often the path chosen will simply be the shortest possible one, but a different angular path may be chosen to avoid certain portions of the brain, at the judgment of the surgeon. The patient is indexed into the scanner throat g so that its scanning plane h is at the point of interest, with the carriage 80 slided to an estimated proper position, the arm 90 extended, and the guide-holder 95 in place. Preferably, an instrument guide 98 is screwed into the guide-holder 95; its decreased bore size provides increased accuracy. The positions of the carriage 80, arm 90 and guide-holder 95 are adjusted until the guide bore 99 is approximately at the plane of interest and the desired point of entrance through the skull for the chosen path. Then a scan may be made to determine whether the guide bore 99 is in the scanning plane of interest and whether it is directed along the desired path, as shown in FIG. 4, which is a scanner representation of the skull k with an interior brain lesion m and the guide-holder 95 with the instrument guide 98 in place. Repeated scanning and readjustment may be required until exact positioning is achieved. In the preferred embodiment, where the guide-holder provided has a density of the order of and slightly greater than that of the brain tissue, the guide-holder, including its path-directing bore, may be seen on the same grey scale scanner representation (substantially the same "level" and "window") as the brain lesion or other abnormality, the guide-holder appearing as solid white and its bore as black. But, where the density of the guide-holder substantially differs from that of body tissue, such as having a density substantially greater than the brain or other body tissue under study, it may be necessary to temporarily mark the position of either the point of interest or the guide-holder on the exterior of the CRT screen, such as by utilizing a grease pencil, and then change the grey scale by adjusting the "level" and/or the window to clearly show the other. This may be necessary due to artifacts caused by a high density guide-holder which interferes with the grey scale representation of the brain; changing the grey scale may avoid the artifacts. Though good results may be available utilizing such a relatively dense material for the guide-holder, it clearly will be more convenient to avoid the necessity of such an adjustment of the grey scale.

Next, the scanner cradle c may be moved out of the throat g and the point of entrance marked on the patient's head at the location of the guide bore 99. Afterward, by loosening the thumbscrew 92 in the outer end of the arm 90, the riser post 94 may be rotated to swivel the guide-holder 95 away from the marked point of entrance, to permit an incision to be made in the skin at that point. The guide-holder 95 may then be rotated back to the incised point, and a drill guide 98 threaded into the guide-holder bore 97; then a twist drill is inserted through the drill guide 98 and a bore is made in the patient's skull at the point of entrance. A scan preliminary to drilling may be desirable to recheck the orientation of the guide bore 99, for most accurate results.

Finally, a needle guide 98 is threaded into the guide-holder bore 97, replacing the drill guide. At this point, a scan may be performed at the plane of interest to assure that the guide-holder 95 is properly positioned with the needle guide bore 99 in the plane of interest on a line directed to the point of interest, as shown in FIG. 4. When exact placement is achieved, a needle n of the type suitable for performing the surgical procedure, is inserted, through the needle guide 98 and skull bore, into the brain tissue. The insertion distance required may be determined by consulting the cathode ray tube display and utilizing the known ratio of scanner image to real image size to calculate the linear distance; or for greater accuracy, the needle may be inserted into the brain approximately to the required depth and one or more scans performed in the plane of interest to determine whether the needle is to the correct depth, as well as along the desired path, as shown in FIG. 5. Once it has been determined that the needle is at the correct depth and position, the desired surgical procedure is performed.

Summarizing, the method of carrying out the present invention may be described as a method for performing surgical procedures on the brain through a bore in the skull to a point of procedure or interest in the interior of the brain by utilizing a scanner of the type which utilizes computer-assisted tomography to develop indexed parallel planar sectional representations of the head. The steps in the method include first securing the patient's head in a fixed position relative to the indexable cradle of the scanner and preliminarily scanning the head to develop as many sectional representations as may be necessary to select an indexed plane of interest at which a chosen point of procedure is located. Then the guide-path-establishing instrument holder is positioned outward of the skull in the plane of interest so that its guide path may become visible on a developed sectional representation of the head. Scanning at the plane of interest and further adjustment of the instrument holder confirms its position for such guidance of the instrument or needle along the selected straight-line path to the point of procedure. Finally, a bore is drilled through the skull at the point of interest, preferably guided by the bore of the instrument holder, and the surgical needle is inserted through the instrument holder bore and skull bore to be guided by the holder to the point of procedure.

Where the exact depth of the surgical instrument is critical, the needle or other instrument may be inserted to a proposed depth and then a scan performed at the plane of interest with the instrument so inserted to confirm that it is inserted to the point of procedure.

It has been found to be most desirable in securing the patient's head in fixed position relative to the scanner cradle to support the rear of the head behind the ears substantially at the mastoid processes, and to support the front of the head beneath the eyes at the cheekbone area, either at the zygomatic arches or at the maxilla. This low position of mounting on the head leaves the entire upper portion of the head free of any obstruction which might cause artifacts on the scans. As will be obvious, such combination of a ring-like member with first adjustable rest means to conform to and support the head at the mastoid processes and second adjustable rest means to conform to and support the head at the cheekbone area may be utilized as head-holding apparatus for restraint to any adjacent support fixed relative to the patient's body during any surgical procedure performed on the upper portion of the head.

Other advantages of the present invention will be apparent to persons familiar with the problems of cranial surgery. Fixing the guide-holder to the head-holding ring establishes an accurate guide path to the point of interest. By providing the track and carriage mechanism at the upper end of the ring, the guide-holder may be moved to either side of the head or to its center so that the selected straight-line path to the point of interest may be the most direct path possible; or where the brain tissue along a direct path is thought to be too delicate to attempt insertion of a needle through it, the carriage 80 may be slided around the head and fixed at a different position, to permit operation along a different angular path. Mounting the ring at the location beneath the eyes and ears assures that as much of the upper portion of the head as possible is unobstructed by metal or other dense objects which may cause artifacts on the scan; they are further avoided by use of the radiolucent foam and the polymethylmethacrylate plastic for the head rests and low density material such as the polymethylmethacrylate for the arm 90. The slide clamping-type mount of the ring 30 to the ring mount 20 permits the patient's head to be rotated to a desired angular position, for example, with the patient lying on his side. In such case, the rests may nevertheless comfortably and securely support the head at the mastoid process, behind the ear, and beneath the eyes, substantially at the cheekbone area.

Modifications of the present invention will be apparent to persons skilled in the art. For example, another type of adjustable rest means to conform to and support the head behind the ears substantially at the mastoid processes and beneath the eyes at substantially the cheekbone area may be utilized. Likewise, other means mounted to the ring-like member and angularly adjustable relative thereto may be utilized to support an instrument utilized for the surgical procedure on the head. From these examples, other modifications will suggest themselves.

We claim:

1. Apparatus for use in guidance of insertion of surgical instruments into a patient's body by use of computer-assisted tomography equipment which provides a plurality of scans in parallel planes, including a scanning throat and a body-supporting cradle axially positionable relative thereto, the apparatus comprising
    frame-like patient restraint means including means for rigid securement to the body-supporting cradle and having an arcuate track portion in a plane parallel to the planes of such scans, said frame-like means being smaller in its outer dimension than the scanning throat, and surgical instrument support structure mounted adjustably along the arcuate track portion and projecting away from the plane thereof and including an instrument guide-holder having bore means adjustably securable in a plane parallel to such plane, to slidably accept such a surgical instrument, said guide-holder and that portion of the instrument support structure adjacent thereto being constructed of material having a density substantially of the order of that of body tissue, whereby the guide-holder and the axis of its bore means may be shown on such a computer assisted tomography scan.

2. For use in the insertion of surgical instruments into brain tissue of the upper portion of the head, the apparatus defined in claim 1, wherein said frame-like patient restraint means is of sufficient interior dimension to accommodate a patient's head, and includes projecting away from such plane first adjustable rest means to conform to and support the head behind the ears substantially at the mastoid processes, and second adjustable rest means to conform to and support the head beneath the eyes substantially at the cheekbone area.

3. Apparatus for use in guidance of insertion of an instrument into brain tissue by use of computer-assisted tomography equipment of the type including a substantially horizontal body-supporting cradle positionable relative to the vertical throat of a scanner which provides a plurality of computer-assisted tomography scans in parallel planes, the cradle having a base portion, comprising ring-mount means securable by its lower side to such cradle base portion and receiving its upper side a vertical ring-like member of sufficient interior dimensions to accommodate the patient's head and of such outer dimension as to be accommodated within the throat of the scanner, the ring-like member being formed substantially in a plane and having projecting to one side of such plane a first pair of rests adjustably positionable to conform to and support the head behind the ears substantially at the mastoid processes, and a second pair of rests adjustably positionable to conform to and support the head beneath the eyes substantially at the cheekbone area, said ring-like member including track means positioned between said second pair of rests, said track means being arcuate in the plane of the ring-like member, the apparatus further comprising instrument support structure carriage-mounted to the arcuate track means of the ring-like member and including arm means projecting perpendicularly from the ring-like member, and an instrument guide-holder adjustably supported by the arm means and having bore means, whose axis is in a plane parallel to the ring-like member, to slidably accept such an instrument for insertion into brain tissue, the guide-holder and that portion of the arm means adjacent thereto being constructed of material having such density that such guide-holder and its bore means may be shown on such scans.

4. The apparatus defined in claim 3, wherein such density of the guide-holder is substantially of the order of and greater than the density of such brain tissue.

5. The apparatus defined in claim 3, wherein said guide-holder means includes a fixed diameter bore portion and a plurality of replaceable inserts axially supportable therein, each insert being provided with a concentric bore smaller than said fixed diameter bore portion, whereby instruments of different diameters may be guided precisely in the smaller bore of said inserts.

* * * * *

UNITED STATES PATENT AND TRADEMARK OFFICE
CERTIFICATE OF CORRECTION

PATENT NO. : 4,465,069

DATED : August 14, 1984

INVENTOR(S) : Jean Y. Barbier et al.

It is certified that error appears in the above-identified patent and that said Letters Patent is hereby corrected as shown below:

On the title page, title of invention should read

-- SURGICAL GUIDANCE APPARATUS FOR USE WITH CAT SCANNER --.

Column 2, line 7, "unit" should be ---until---
Column 4, line 30, "of" should ---on---
Column 4, line 44, "arcylic" should be ---acrylic---
Column 4, line 61, "if" should be ---is---
Column 9, line 40, after, "receiving" insert ---on---

Signed and Sealed this

Twelfth Day of March 1985

[SEAL]

Attest:

DONALD J. QUIGG

*Attesting Officer*  *Acting Commissioner of Patents and Trademarks*